(12) United States Patent
Lee et al.

(10) Patent No.: US 11,834,533 B2
(45) Date of Patent: Dec. 5, 2023

(54) POLYMER COMPOSITION

(71) Applicant: LG HOUSEHOLD & HEALTH CARE LTD., Seoul (KR)

(72) Inventors: Whonhee Lee, Seoul (KR); WooSun Shim, Seoul (KR); DoHyuk Yoo, Seoul (KR); SeWon Yeo, Seoul (KR); HaeSeok Chae, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 246 days.

(21) Appl. No.: 17/078,667

(22) Filed: Oct. 23, 2020

(65) Prior Publication Data

US 2021/0122848 A1 Apr. 29, 2021

(30) Foreign Application Priority Data

Oct. 25, 2019 (KR) .................. 10-2019-0133542
Oct. 25, 2019 (KR) .................. 10-2019-0133543

(51) Int. Cl.
| | |
|---|---|
| *A61K 8/81* | (2006.01) |
| *C08F 20/14* | (2006.01) |
| *C08F 20/56* | (2006.01) |
| *C08F 2/22* | (2006.01) |

(52) U.S. Cl.
CPC .......... *C08F 20/14* (2013.01); *A61K 8/8152* (2013.01); *A61K 8/8158* (2013.01); *C08F 2/22* (2013.01); *C08F 20/56* (2013.01)

(58) Field of Classification Search
None
See application file for complete search history.

(56) References Cited

U.S. PATENT DOCUMENTS

| | | | |
|---|---|---|---|
| 6,335,005 B1 * | 1/2002 | Muller | A61Q 3/02 524/460 |
| 2003/0096131 A1 * | 5/2003 | Beavers | A61L 31/10 428/522 |

FOREIGN PATENT DOCUMENTS

| | | | |
|---|---|---|---|
| JP | 2002 220319 | * | 8/2002 |
| JP | 2005 089438 | * | 4/2005 |
| KR | 10-2013-0029318 A | | 3/2013 |
| KR | 10-2016-0073323 A | | 6/2016 |

* cited by examiner

*Primary Examiner* — Brian Gulledge
(74) *Attorney, Agent, or Firm* — Birch, Stewart, Kolasch & Birch, LLP

(57) ABSTRACT

The present application relates to a polymer composition, a film-forming agent, a cosmetic composition and a method of preparing a polymer composition. The present application is directed to providing a polymer composition, which has excellent oil resistance and is capable of forming a cosmetic or the like that has no smudging and no powder flaking during use and a film-forming agent and a cosmetic manufactured using the same.

15 Claims, 4 Drawing Sheets

POLYMER COMPOSITION

CROSS-REFERENCE TO RELATED APPLICATION

This application claims priority to and the benefit of Korean Patent Application No. 10-2019-0133543 and Korean Patent Application No. 10-2019-0133542, filed on Oct. 25, 2019, the disclosures of which are incorporated herein by reference in their entirety.

BACKGROUND

1. Field of the Invention

The present application relates to a polymer composition, a film-forming agent, a cosmetic composition and a method of preparing a polymer composition.

2. Discussion of Related Art

Functional polymers are sometimes required for the manufacture of cosmetics or medicines. For example, functional polymers are required for the manufacture of cosmetics or medicines that are applied directly to the skin, including mascara and the like.

Such functional polymers may be required to have oil resistance, which is resistance to oily components such as sebum and the like and also have appropriate applicability or film forming ability.

In addition, the functional polymers may be required to prevent cosmetics or medicines from smudging due to sebum, tears, sweat and the like and powder flaking during use.

Additionally, since cosmetics or medicines are usually used while being in direct contact with the human body, the functional polymers should not contain harmful materials.

SUMMARY OF THE INVENTION

The present application provides a polymer composition, a film-forming agent, a cosmetic composition and a method of preparing a polymer composition. The present application is directed to providing a polymer composition, which has excellent oil resistance and is capable of forming a cosmetic or the like that has no smudging and no powder flaking during use and a film-forming agent and a cosmetic manufactured using the same.

A polymer composition of the present application may consist of only a polymer to be described below or include a polymer to be described below and other components.

For example, the content of the polymer to be described below in the polymer composition may be about 5% by weight or more, 10% by weight or more, 15% by weight or more, 20% by weight or more, 25% by weight or more, 30% by weight or more, 35% by weight or more, 40% by weight or more, 45% by weight or more, 50% by weight or more, 55% by weight or more, 60% by weight or more, 65% by weight or more, 70% by weight or more, 75% by weight or more, 80% by weight or more, 85% by weight or more, 90% by weight or more, or 95% by weight or more. Since the polymer composition may consist of only the polymer, the content of the polymer may be about 100% by weight or less, 99% by weight or less, or 98% by weight or less. The content of the polymer is a content calculated excluding the weight of a solvent when components are dispersed or dissolved in the solvent to prepare the polymer composition.

The polymer included in the polymer composition includes specific types of monomer polymerization units and a ratio of the polymerization units may be adjusted. By controlling the types and ratio of monomers, a polymer composition, which has desired physical properties, for example, oil resistance and is capable of forming a film-forming agent, a cosmetic, or a medicine that is prevented from smudging and powder flaking during use, may be obtained.

As used herein, the content (e.g., % by weight, parts by weight, etc.) of any monomer may refer to a content of any monomer applied in the preparation of the polymer or a content of any monomer polymerization unit included in the polymer.

The polymer may include a first monomer polymerization unit having a solubility parameter of 11 $(cal/cm^3)^{1/2}$ or more and a second monomer polymerization unit having a solubility parameter of less than 11 $(cal/cm^3)^{1/2}$.

In the specification, any monomer or compound polymerization unit refers to any monomer or compound included as a monomer unit in a polymer through polymerization thereof.

The term "solubility parameter" refers to a solubility parameter of a homopolymer produced by polymerizing the relevant monomer and accordingly, levels of hydrophilicity and hydrophobicity of the monomer may be determined by the solubility parameter. A method of obtaining a solubility parameter is not particularly limited and a method known in the art may be used. For example, the solubility parameter may be calculated and obtained by a method known as a so-called group-contribution method of Hoftyzer and Van Krevelen in the art.

The first monomer is relatively hydrophilic compared to the second monomer and the hydrophilicity of the first monomer may contribute to ensuring desired oil resistance. In another example, the first monomer may have a solubility parameter of about 11.5 $(cal/cm^3)^{1/2}$ or more, 12 $(cal/cm^3)^{1/2}$ or more, 12.5 $(cal/cm^3)^{1/2}$ or more, 13 $(cal/cm^3)^{1/2}$ or more, 13.5 $(cal/cm^3)^{1/2}$ or more, or 14 $(cal/cm^3)^{1/2}$ or more or about 20 $(cal/cm^3)^{1/2}$ or less, 19 $(cal/cm^3)^{1/2}$ or less, 18 $(cal/cm^3)^{1/2}$ or less, 17 $(cal/cm^3)^{1/2}$ or less, 16 $(cal/cm^3)^{1/2}$ or less, 15 $(cal/cm^3)^{1/2}$ or less, 14 $(cal/cm^3)^{1/2}$ or less, 13 $(cal/cm^3)^{1/2}$ or less, or 12.5 $(cal/cm^3)^{1/2}$ or less.

As the first monomer, a monomer appropriately selected from among monomers known to have a solubility parameter within the above-described range may be used.

For example, the first monomer may have a glass transition temperature (hereinafter, referred to as "Tg") of −40° C. to 400° C. As used herein, the Tg of a monomer is a Tg known for a homopolymer made of the relevant monomer.

In another example, the first monomer may have a Tg of about −35° C. or more, −30° C. or more, −25° C. or more, −20° C. or more, −15° C. or more, −10° C. or more, −5° C. or more, 0° C. or more, 10° C. or more, 20° C. or more, 30° C. or more, 40° C. or more, 50° C. or more, 60° C. or more, 70° C. or more, 80° C. or more, 90° C. or more, 100° C. or more, 110° C. or more, 120° C. or more, 130° C. or more, 140° C. or more, 150° C. or more, 160° C. or more, 170° C. or more, 180° C. or more, 190° C. or more, 200° C. or more, or 210° C. or more or about 390° C. or less, 380° C. or less, 370° C. or less, 360° C. or less, 350° C. or less, 340° C. or less, 330° C. or less, 320° C. or less, 310° C. or less, 300° C. or less, 290° C. or less, 280° C. or less, 270° C. or less, 260° C. or less, 250° C. or less, 240° C. or less, 230° C. or less, 220° C. or less, 210° C. or less, 200° C. or less, 190° C. or less, 180° C. or less, 170° C. or less, 160° C. or less, 150° C. or less, 140° C. or less, 130° C. or less, 120° C. or less, 110° C. or less, 100° C. or less, 90° C. or less, 80° C. or less, 70° C. or less, 60° C. or less, 50° C. or less, 40° C. or less, 30° C. or less, 20° C. or less, 10° C. or less, 5° C. or less, 0° C. or less, −5° C. or less, or −10° C. or less.

As the first monomer, for example, a hydroxyl group-containing monomer such as 2-hydroxyalkyl (meth)acrylate; a polymeric heterocyclic monomer such as vinylpyrrolidone; a (meth)acrylamide-based monomer such as (meth)acrylamide, N-alkyl (meth)acrylamide, or N,N-dialkyl (meth)acrylamide; an acidic monomer such as (meth)acrylic acid, maleic acid, or itaconic acid; glyceryl (meth)acrylate; or an alkylene oxide unit-containing monomer may be used. Among the above-listed monomers, the acidic monomer may be suitable as the first monomer.

As used herein, the term "(meth)acryl" refers to acryl or methacryl.

As used herein, the term "alkyl or alkyl group" refers to, unless otherwise specified, a straight, branched, or cyclic alkyl or alkyl group having 1 to 20 carbon atoms, 1 to 16 carbon atoms, 1 to 12 carbon atoms, 1 to 8 carbon atoms, or 1 to 4 carbon atoms. The alkyl or alkyl group may be an alkyl or alkyl group optionally substituted with one or more substituents or an unsubstituted alkyl or alkyl group.

As the alkylene oxide unit-containing monomer, for example, a monomer represented by the following Chemical Formula 1 or 2 may be exemplified:

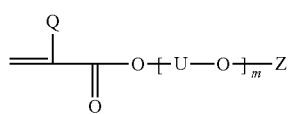

[Chemical Formula 1]

In Chemical Formula 1, Q is hydrogen or an alkyl group, U is an alkylene group, Z is hydrogen or an alkyl group and m is a random number;

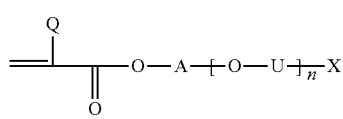

[Chemical Formula 2]

In Chemical Formula 2, Q is hydrogen or an alkyl group, A and U are each independently an alkylene group, X is hydrogen, an alkyl group, a hydroxyl group, or a cyano group and n is a random number.

In Chemical Formulas 1 and 2, as the alkylene group, an alkylene group having 1 to 20 carbon atoms, 1 to 16 carbon atoms, 1 to 12 carbon atoms, 1 to 8 carbon atoms, or 1 to 4 carbon atoms may be exemplified. The alkylene group may be straight, branched, or cyclic. The alkylene group may be optionally substituted with one or more substituents.

In Chemical Formulas 1 and 2, as the alkyl groups present in Q and Z, an alkyl group having 1 to 20 carbon atoms, 1 to 16 carbon atoms, 1 to 12 carbon atoms, 1 to 8 carbon atoms, or 1 to 4 carbon atoms may be exemplified. The alkyl group may be straight, branched, or cyclic. In addition, the alkyl group may be optionally substituted with one or more substituents.

In Chemical Formulas 1 and 2, m and n are random numbers and may each independently be, for example, a number ranging from 1 to 100, 1 to 90, 1 to 80, 1 to 70, 1 to 60, 1 to 50, 1 to 40, 1 to 30, 1 to 20, 1 to 16, or 1 to 12.

In an example, as the first monomer, a compound represented by Chemical Formula 1, in which Q is hydrogen or a C1 to C4 alkyl group, U is a C1 to C4 alkylene group, Z is hydrogen or a C1 to C4 alkyl group and m is a number ranging from 1 to 30, may be used, but the present application is not limited thereto.

The content of the first monomer polymerization unit in the polymer may be controlled in consideration of desired physical properties, for example, oil resistance and the like.

For example, the content of the first monomer polymerization unit among the entire polymerization units included in the polymer may range from about 1 to 40% by weight. In another example, the content may be about 1.5% by weight or more, 2% by weight or more, 2.5% by weight or more, 3% by weight or more, 3.5% by weight or more, 4.5% by weight or more, 5% by weight or more, 5.5% by weight or more, 6% by weight or more, 6.5% by weight or more, 7% by weight or more, 7.5% by weight or more, 8% by weight or more, 8.5% by weight or more, 9% by weight or more, 9.5% by weight or more, 10% by weight or more, 11% by weight or more, 12% by weight or more, 13% by weight or more, 14% by weight or more, or 14.5% by weight or more or about 39% by weight or less, 38% by weight or less, 37% by weight or less, 36% by weight or less, 35% by weight or less, 34% by weight or less, 33% by weight or less, 32% by weight or less, 31% by weight or less, 30% by weight or less, 29% by weight or less, 28% by weight or less, 27% by weight or less, 26% by weight or less, 25% by weight or less, 24% by weight or less, 23% by weight or less, 22% by weight or less, 21% by weight or less, 20% by weight or less, 19% by weight or less, 18% by weight or less, 17% by weight or less, 16% by weight or less, 15% by weight or less, 14% by weight or less, 13% by weight or less, 12% by weight or less, 11% by weight or less, 10% by weight or less, 9% by weight or less, 8% by weight or less, 7% by weight or less, 6% by weight or less, or 5.5% by weight or less. Under such a content, a polymer composition with desired physical properties may be provided. For example, as the content of the first monomer polymerization unit increases, it may be advantageous in terms of oil resistance described above. However, since the first monomer is relatively hydrophilic, the first monomer, for example, causes a thickening effect in an emulsion polymerization process under an aqueous solvent and thus it is not easy to include an appropriate level of the first monomer in the polymer. However, for example, when a so-called seed emulsion polymerization method is used, a polymer composition including a polymer having a relatively high content of the first monomer as described above may be effectively prepared.

Therefore, in an example, the polymer may be a seed emulsion polymer. The seed emulsion polymer refers to a polymer produced by seed emulsion polymerization. The seed emulsion polymerization may be performed in a manner described below in the specification.

The second monomer is relatively hydrophobic compared to the first monomer. In another example, the second monomer may have a solubility parameter of about 10.5 (cal/cm')$^{1/2}$ or less, 10 (cal/cm$^3$)$^{1/2}$ or less, 9.5 (cal/cm')$^{1/2}$ or less, or 9 (cal/cm$^3$)$^{1/2}$ or less or about 4 (cal/cm$^3$)$^{1/2}$ or more, 5 (cal/cm$^3$)$^{1/2}$ or more, 6 (cal/cm$^3$)$^{1/2}$ or more, 7 (cal/cm$^3$)$^{1/2}$ or more, 8 (cal/cm$^3$)$^{1/2}$ or more, 8.5 (cal/cm$^3$)$^{1/2}$ or more, 9 (cal/cm$^3$)$^{1/2}$ or more, 9.5 (cal/cm$^3$)$^{1/2}$ or more, or 10 (cal/cm$^3$)$^{1/2}$ or more.

As the second monomer, a monomer selected appropriately from among monomers known to have a solubility parameter within the above-described range may be used.

By being included together with the first monomer in the polymer, the second monomer may contribute to forming a film-forming agent, a cosmetic, or a medicine that ensures oil resistance and has no powder flaking or no smudging.

As a monomer that is usable as the second monomer, alkyl (meth)acrylate or aromatic (meth)acrylate may be exemplified. As used herein, the term "(meth)acrylate" may refer to an acrylate or methacrylate.

As an alkyl group included in the alkyl (meth)acrylate, a straight, branched, or cyclic alkyl group having 2 to 20 carbon atoms, 2 to 16 carbon atoms, 2 to 12 carbon atoms, or 2 to 8 carbon atoms may be exemplified and the alkyl group may be optionally substituted with one or more substituents. As the alkyl (meth)acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, 2-ethylhexyl (meth)acrylate, 2-ethylbutyl (meth)acrylate, n-octyl (meth)acrylate, isobornyl (meth)acrylate, isooctyl (meth)acrylate, isononyl (meth)acrylate, or lauryl (meth)acrylate may be exemplified, but the present application is not limited thereto.

As the aromatic (meth)acrylate, aryl (meth)acrylate or arylalkyl (meth)acrylate may be exemplified. In this case, an aryl group of the aryl or arylalkyl may be, for example, an aryl group having 6 to 24 carbon atoms, 6 to 18 carbon atoms, or 6 to 12 carbon atoms. In addition, an alkyl group of the arylalkyl may be, for example, an alkyl group having 1 to 20 carbon atoms, 1 to 16 carbon atoms, 1 to 12 carbon atoms, 1 to 8 carbon atoms, or 1 to 4 carbon atoms. The alkyl group may be straight, branched, or cyclic and the alkyl group or aryl group may be optionally substituted with one or more substituents.

As the aryl group or arylalkyl group, a phenyl group, a phenylethyl group, a phenylpropyl group, or a naphthyl group may be exemplified, but the present application is not limited thereto.

As the second monomer, for example, a monomer represented by the following Chemical Formula 3 may be used.

[Chemical Formula 3]

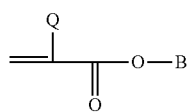

In Chemical Formula 3, Q is hydrogen or an alkyl group and B is a straight or branched alkyl group having 2 or more carbon atoms, an alicyclic hydrocarbon group, or an aromatic substituent such as the aryl group or the arylalkyl group.

In Chemical Formula 3, as the alkyl group present in Q, an alkyl group having 1 to 20 carbon atoms, 1 to 16 carbon atoms, 1 to 12 carbon atoms, 1 to 8 carbon atoms, or 1 to 4 carbon atoms may be exemplified. The alkyl group may be straight, branched, or cyclic. The alkyl group may be optionally substituted with one or more substituents.

In Chemical Formula 3, B may be a straight or branched alkyl group having 2 or more carbon atoms, 2 to 20 carbon atoms, 2 to 16 carbon atoms, 2 to 12 carbon atoms, or 2 to 10 carbon atoms.

In another example, B in Chemical Formula 3 may be an alicyclic hydrocarbon group, for example, an alicyclic hydrocarbon group having 3 to 20 carbon atoms, 3 to 16 carbon atoms, or 6 to 12 carbon atoms and as the hydrocarbon group, an alicyclic alkyl group having 3 to 20 carbon atoms, 3 to 16 carbon atoms, or 6 to 12 carbon atoms, such as a cyclohexyl group, an isobornyl group, or the like, may be exemplified. A compound having the alicyclic hydrocarbon group is also known as a relatively hydrophobic compound.

To ensure desired physical properties, a mixture of at least two types of monomers may be used as the second monomer.

For example, as the second monomer, a monomer A having a relatively high glass transition temperature (hereinafter, referred to as "Tg") and a monomer B having a relatively low Tg may be used. Therefore, for example, the polymer may include a monomer A polymerization unit having a Tg of 20° C. or more and a monomer B polymerization unit having a Tg of less than 20° C. as the second monomer polymerization unit.

As used herein, the Tg of a monomer is a Tg known for a homopolymer made of the monomer.

In another example, the monomer A may have a Tg of about 25° C. or more, 30° C. or more, 35° C. or more, 40° C. or more, 45° C. or more, 50° C. or more, 55° C. or more, 60° C. or more, 65° C. or more, 70° C. or more, 75° C. or more, 80° C. or more, 85° C. or more, 90° C. or more, 95° C. or more, or 100° C. or more or about 150° C. or less, 145° C. or less, 140° C. or less, 135° C. or less, 130° C. or less, 125° C. or less, 120° C. or less, 115° C. or less, 110° C. or less, 105° C. or less, 100° C. or less, 95° C. or less, 90° C. or less, 85° C. or less, 80° C. or less, 75° C. or less, or 70° C. or less. In addition, in another example, the monomer B may have a Tg of 15° C. or less, 10° C. or less, 5° C. or less, 0° C. or less, −5° C. or less, −10° C. or less, −15° C. or less, −20° C. or less, −25° C. or less, −30° C. or less, −35° C. or less, −40° C. or less, or −45° C. or less or −150° C. or more, −145° C. or more, −140° C. or more, −135° C. or more, −130° C. or more, −125° C. or more, −120° C. or more, −115° C. or more, −110° C. or more, −105° C. or more, −100° C. or more, −95° C. or more, −90° C. or more, −85° C. or more, −80° C. or more, −75° C. or more, −70° C. or more, −65° C. or more, −60° C. or more, or −55° C. or more.

When a mixture of two types of monomers is used as the second monomer as described above, the overall Tg of the polymer may be maintained at an appropriate level and it is advantageous for forming a polymer with both oil resistance and other desired properties (e.g., anti-smudging and anti-powder flaking properties).

As the monomer A and the monomer B, appropriate types of monomers may be selected from among the monomers described above as the second monomer in consideration of the Tg of the monomer.

For example, as the monomer A, a compound represented by Chemical Formula 3, in which Q is an alkyl group, for example, an alkyl group having 1 to 20 carbon atoms, 1 to 16 carbon atoms, 1 to 12 carbon atoms, 1 to 8 carbon atoms, or 1 to 4 carbon atoms or a methyl group and B is a straight or branched alkyl group having 2 or more carbon atoms, may be used. In this case, the alkyl group of B may be a straight or branched alkyl group having 2 to 4 carbon atoms.

For example, as the monomer B, a compound represented by Chemical Formula 3, in which Q is hydrogen and B is a straight or branched alkyl group having 2 or more carbon atoms, 4 or more carbon atoms, or 6 or more carbon atoms, may be used. In this case, the upper limit of carbon number of the alkyl group of B is not particularly limited and may be, for example, about 20, 18, 16, 14, 12, or 10.

The content of the second monomer polymerization unit in the polymer may range from 150 to 4,000 parts by weight relative to 100 parts by weight of the first monomer polymerization unit. In another example, the content may be about 200 parts by weight or more, 250 parts by weight or more, 300 parts by weight or more, 350 parts by weight or more, 400 parts by weight or more, 450 parts by weight or more, 500 parts by weight or more, 550 parts by weight or more, 600 parts by weight or more, 650 parts by weight or more, 700 parts by weight or more, 750 parts by weight or more, 800 parts by weight or more, 850 parts by weight or more, 900 parts by weight or more, 950 parts by weight or more, 1,000 parts by weight or more, 1,100 parts by weight or more, 1,200 parts by weight or more, 1,300 parts by weight or more, 1,400 parts by weight or more, 1,500 parts by weight or more, 1,600 parts by weight or more, 1,700 parts by weight or more, 1,800 parts by weight or more, or 1,850 parts by weight or more or about 2,350 parts by weight or less, 2,300 parts by weight or less, 2,250 parts by weight or less, 2,200 parts by weight or less, 2,150 parts by weight or less, 2,100 parts by weight or less, 2,050 parts by weight or less, 2,000 parts by weight or less, 1,950 parts by weight or less, 1,900 parts by weight or less, 1,800 parts by weight or less, 1,700 parts by weight or less, 1,600 parts by weight or less, 1,500 parts by weight or less, 1,400 parts by weight or less, 1,300 parts by weight or less, 1,200 parts by weight or less, 1,100 parts by weight or less, 1,000 parts by weight or less, 900 parts by weight or less, 800 parts by weight or less, 700 parts by weight or less, or 600 parts by weight or less.

When the monomer A and the monomer B are applied as the second monomer polymerization unit, a weight ratio (A/B) of the monomer A polymerization unit and the monomer B polymerization unit may range from 0.25 to 5. In another example, the weight ratio (A/B) may be about 0.3 or more, 0.35 or more, 0.4 or more, 0.45 or more, 0.5 or more, 0.55 or more, 0.6 or more, 0.65 or more, 0.7 or more, 0.75 or more, 0.8 or more, 0.85 or more, 0.9 or more, 0.95 or more, 1.0 or more, 1.5 or more, or 2 or more or about 4.5 or less, 4 or less, 3.5 or less, 3 or less, 2.5 or less, 2 or less, 1.5 or less, 1 or less, 0.95 or less, 0.9 or less, 0.85 or less, 0.8 or less, 0.75 or less, or 0.7 or less.

In addition to the above-described first monomer and second monomer, the polymer may appropriately include additional known monomers within the range not impairing desired physical properties.

As described above, the polymer of the present application may have, for example, a Tg of about −30° C. to 30° C. In another example, the polymer may have a Tg of about −25° C. or more, −20° C. or more, −15° C. or more, or −10° C. or more or about 25° C. or less, 20° C. or less, 15° C. or less, 10° C. or less, 5° C. or less, 0° C. or less, or −5° C. or less. The Tg is a theoretical value obtained from the monomer composition of the polymer through the so-called Fox equation. The above-described Tg may be useful, for example, when the polymer is applied as a film-forming agent for a cosmetic or a medicine. By using the polymer having a Tg within the above-described range, it may be possible to efficiently form a coating having excellent oil resistance without sticking, smudging, powder flaking and the like occurring.

In the present application, the polymer may have a weight-average molecular weight (Mw) of 100,000 to 2,000,000. As used herein, the weight-average molecular weight may be, for example, a conversion value with respect to standard polystyrene, which is measured through gel permeation chromatography (GPC) and the term "molecular weight" may refer to, unless otherwise specified, a weight-average molecular weight. The above-described molecular weight (Mw) may be useful, for example, when the polymer is applied as a film-forming agent. By using the polymer having a molecular weight (Mw) within the above-described range, it may be possible to efficiently form a coating having excellent oil resistance without sticking, smudging, powder flaking and the like occurring.

In another example, the molecular weight (Mw) may be about 150,000 or more, 200,000 or more, 250,000 or more, 300,000 or more, 350,000 or more, 400,000 or more, 450,000 or more, or 500,000 or more or about 1,900,000 or less, 1,800,000 or less, 1,700,000 or less, 1,600,000 or less, 1,500,000 or less, 1,400,000 or less, 1,300,000 or less, 1,200,000 or less, 1,100,000 or less, 1,000,000 or less, 900,000 or less, 800,000 or less, or 700,000 or less.

The polymer composition of the present application, which includes the above-described polymer, may include no methanol or a minimum amount of methanol. For example, the amount of methanol in the polymer composition may be about 30 ppm or less, 25 ppm or less, 20 ppm or less, 15 ppm or less, 10 ppm or less, 5 ppm or less, 4 ppm or less, 3 ppm or less, 2 ppm or less, 1 ppm or less, or 0.5 ppm or less. That is, in the case of the polymer known to manufacture a film-forming agent or the like, the types and ratio of monomers are controlled to adjust Tg and the like and among these monomers known as the monomer, methanol is produced by hydrolysis and the like. For example, methyl (meth)acrylate, which is frequently applied to adjust Tg in the preparation of a polymer for forming a film-forming agent, produces methanol by hydrolysis and the like. The produced methanol produces formaldehyde that is a representative harmful material in a polymer composition, a coating-forming agent, a cosmetic, or a medicine. However, in the present application, as monomers constituting the polymer, a methanol-producing monomer may not be used, or the content thereof may be minimized, thereby providing a polymer composition, a film-forming agent, a cosmetic, or a medicine, all of which include no methanol or a minimum amount of methanol. However, since the methanol-producing monomer is a monomer known to be very effective for adjusting physical properties, such as Tg and the like, of the polymer, it is not easy to achieve desired physical properties without using this monomer. However, in the present application, by using the above-described types of first and second monomers, monomer A and monomer B, a polymer composition and the like, which have desired physical properties while including no methanol or a small amount of methanol may be provided. Since it is most appropriate that methanol is not included in the polymer composition, the lower limit of a methanol content may be about 0 ppm.

Since the polymer composition of the present application includes no methanol or a minimum amount of methanol, formaldehyde that is a harmful material produced by methanol is also not included or minimally included. For example, the amount of formaldehyde in the polymer composition may be about 30 ppm or less, 25 ppm or less, 20 ppm or less, 15 ppm or less, 10 ppm or less, 5 ppm or less, 4 ppm or less, 3 ppm or less, 2 ppm or less, 1 ppm or less, or 0.5 ppm or less. Since it is most appropriate that formaldehyde is not included in the polymer composition, the lower limit of a formaldehyde content may be about 0 ppm.

The above-described methanol and formaldehyde contents are measured by methods to be described in an exemplary embodiment below.

In order to form the polymer composition including the above-described methanol and formaldehyde contents, the polymer may not include a methanol-producing monomer polymerization unit. As a monomer which produces methanol by hydrolysis and the like and is widely used in the manufacture of a film-forming agent, methyl methacrylate, methyl acrylate, or the like is used.

As a relatively hydrophobic monomer (e.g., the second monomer of the present application) or a monomer with a relatively high Tg (e.g., the monomer A of the present application) which is applied to a polymer for forming a film-forming agent or the like, a methyl group-containing monomer such as methyl methacrylate or the like is often used. However, the types of monomers described as the second monomer in the present application do not produce methanol, or even when they produce methanol, a trace amount of methanol is produced. Therefore, it is appropriate to apply the above-described types of monomers as the second monomer, especially, at least the monomer A of the second monomer in the present application.

Therefore, in an example, the polymer may include only the monomer polymerization unit represented by Chemical Formula 3 as the second monomer or monomer A polymerization unit.

For example, the polymer may include, as at least the monomer A polymerization unit, only a compound polymerization unit represented by Chemical Formula 3 in which Q is an alkyl group (e.g., an alkyl group having 1 to 20 carbon atoms, 1 to 16 carbon atoms, 1 to 12 carbon atoms, 1 to 8 carbon atoms, or 1 to 4 carbon atoms) or a methyl group and B is a straight or branched alkyl group having 2 or more carbon atoms. In this case, the alkyl group of B may be a straight or branched alkyl group having 2 to 4 carbon atoms.

The polymer composition of the present application may include only the polymer or include other necessary components in addition to the polymer.

As such necessary components, for example, a formaldehyde-removing agent may be exemplified. As an applicable formaldehyde-removing agent, ammonia, urea, sodium hydrogen sulfite and/or sodium metabisulfite may be exemplified, but the present application is not limited thereto. The content of the formaldehyde-removing agent in the polymer composition may be an appropriate level, for example, about 10 parts by weight or less, 9 parts by weight or less, 8 parts by weight or less, 7 parts by weight or less, 6 parts by weight or less, 5 parts by weight or less, 4 parts by weight or less, or 3 parts by weight or less relative to 100 parts by weight of the polymer. Alternatively, the content of the formaldehyde-removing agent may be about 0 parts by weight or more, more than 0 parts by weight, 0.5 parts by weight or more, 1 part by weight or more, 1.5 parts by weight or more, or 2.5 parts by weight or more relative to 100 parts by weight of the polymer.

The polymer composition may further include necessary additives in addition to the polymer and/or the formaldehyde-removing agent.

As such additives, an oil, a surfactant, purified water, a polyhydric alcohol (e.g., glycerin, propylene glycol, butylene glycol, etc.), an organic powder, an inorganic powder, a UV absorber, a preservative, an antifoaming agent, an antibacterial agent, an antioxidant, a beauty component, a fragrance, a thickener, a gelling agent, a metal soap, a water-soluble polymer, an oil-soluble polymer, a fiber (nylon, rayon, etc.), a pigment and/or a pearling agent may be exemplified, but the present application is not limited thereto.

The polymer composition may be prepared by various known methods, but it is effective to use an emulsion polymerization method in consideration of the formation efficiency and application efficiency of the polymer. For example, an emulsion polymerization method using an aqueous solvent such as water as a continuous phase may be used.

In particular, in order to form a polymer including the above-described first monomer and having a high content of the first monomer polymerization unit, it is effective to use an emulsion polymerization method, especially, a seed emulsion polymerization method. The seed emulsion polymerization is a polymerization method in which a pre-polymerized emulsion polymer with relatively small particles is provided as a seed and homogeneous or heterogeneous monomers are polymerized in the seed to grow the particles. When this method is used, the polymer desired in the present application may be more effectively produced.

The seed emulsion polymerization method may include, for example, a seed polymerization step and a seed growth step.

In an example, the polymerization method may include a first step of performing seed emulsion polymerization of a reaction solution containing a monomer mixture, an aqueous solvent and a surfactant; and a second step of growing a seed produced in the first step by adding a reaction solution containing a monomer mixture to the product produced by the seed emulsion polymerization of the first step and performing emulsion polymerization.

Each of the monomer mixtures used in the first step and the second step may include the above-described first and second monomers and also include the above-described monomer A and monomer B as the second monomer. In this case, the content of each monomer in the monomer mixture may be adjusted so that the polymerization unit is included at the above-described content and, in an example, may be approximately similar to the above-described content of the polymerization unit.

For example, the content of the first monomer in the monomer mixture may range from about 1 to 40% by weight. In another example, the content may be about 1.5% by weight or more, 2% by weight or more, 2.5% by weight or more, 3% by weight or more, 3.5% by weight or more, 4.5% by weight or more, 5% by weight or more, 5.5% by weight or more, 6% by weight or more, 6.5% by weight or more, 7% by weight or more, 7.5% by weight or more, 8% by weight or more, 8.5% by weight or more, 9% by weight or more, 9.5% by weight or more, 10% by weight or more, 11% by weight or more, 12% by weight or more, 13% by weight or more, 14% by weight or more, or 14.5% by weight or more or about 39% by weight or less, 38% by weight or less, 37% by weight or less, 36% by weight or less, 35% by weight or less, 34% by weight or less, 33% by weight or less, 32% by weight or less, 31% by weight or less, 30% by weight or less, 29% by weight or less, 28% by weight or less, 27% by weight or less, 26% by weight or less, 25% by weight or less, 24% by weight or less, 23% by weight or less, 22% by weight or less, 21% by weight or less, 20% by weight or less, 19% by weight or less, 18% by weight or less, 17% by weight or less, 16% by weight or less, 15% by weight or less, 14% by weight or less, 13% by weight or less, 12% by weight or less, 11% by weight or less, 10% by weight or less, 9% by weight or less, 8% by weight or less, 7% by weight or less, 6% by weight or less, or 5.5% by weight or less.

In addition, the second monomer may be included in an amount of 150 to 4,000 parts by weight relative to 100 parts by weight of the first monomer. In another example, the content may be about 200 parts by weight or more, 250 parts by weight or more, 300 parts by weight or more, 350 parts by weight or more, 400 parts by weight or more, 450 parts by weight or more, 500 parts by weight or more, 550 parts by weight or more, 600 parts by weight or more, 650 parts by weight or more, 700 parts by weight or more, 750 parts by weight or more, 800 parts by weight or more, 850 parts by weight or more, 900 parts by weight or more, 950 parts by weight or more, 1,000 parts by weight or more, 1,100 parts by weight or more, 1,200 parts by weight or more, 1,300 parts by weight or more, 1,400 parts by weight or more, 1,500 parts by weight or more, 1,600 parts by weight or more, 1,700 parts by weight or more, 1,800 parts by weight or more, or 1,850 parts by weight or more or about 2,350 parts by weight or less, 2,300 parts by weight or less, 2,250 parts by weight or less, 2,200 parts by weight or less, 2,150 parts by weight or less, 2,100 parts by weight or less, 2,050 parts by weight or less, 2,000 parts by weight or less, 1,950 parts by weight or less, 1,900 parts by weight or less, 1,800 parts by weight or less, 1,700 parts by weight or less, 1,600 parts by weight or less, 1,500 parts by weight or less, 1,400 parts by weight or less, 1,300 parts by weight or less, 1,200 parts by weight or less, 1,100 parts by weight or less, 1,000 parts by weight or less, 900 parts by weight or less, 800 parts by weight or less, 700 parts by weight or less, or 600 parts by weight or less.

In addition, when the monomer A and the monomer B are applied as the second monomer in the monomer mixture, a weight ratio (A/B) of the monomer A and the monomer B may range from 0.25 to 5. In another example, the weight ratio (A/B) may be about 0.3 or more, 0.35 or more, 0.4 or more, 0.45 or more, 0.5 or more, 0.55 or more, 0.6 or more, 0.65 or more, 0.7 or more, 0.75 or more, 0.8 or more, 0.85 or more, 0.9 or more, 0.95 or more, 1.0 or more, 1.5 or more, or 2 or more or about 4.5 or less, 4 or less, 3.5 or less, 3 or less, 2.5 or less, 2 or less, 1.5 or less, 1 or less, 0.95 or less, 0.9 or less, 0.85 or less, 0.8 or less, 0.75 or less, or 0.7 or less.

The above-described contents of the first and second monomers and the monomer A and the monomer B in the monomer mixture may be contents determined based on the sum of all the monomer mixtures applied in the first and second steps. That is, as described below, the polymerization method of the present application may be performed by dispersing monomers and components such as a surfactant and the like in a solvent (aqueous solvent such as water) to prepare a reaction solution, setting aside a part of the reaction solution, performing seed emulsion polymerization of the first step and then adding the set-aside reaction solution in the second step and thus the contents of the monomers may be based on the sum of the monomer mixtures applied in the first and second steps.

For the emulsion polymerization, the monomer mixture is used together with the surfactant. As the surfactant, a surfactant that is known to be applicable in emulsion polymerization may be used. As such a surfactant, an anionic or non-ionic surfactant may be exemplified. Specifically, an anionic surfactant such as sodium lauryl sulfate (SLS), sodium dodecyl benzene sulfate (SDBS), ammonium lauryl sulfate (ALS), sodium cetyl stearyl sulfate, sodium lauryl ether sulfate (SLES), or the like or a non-ionic surfactant known under the name Triton or Tween may be exemplified and one or a mixture of two or more thereof may be used.

The content of the surfactant may be appropriately adjusted according to purpose and the surfactant may be included, for example, in an amount of about 0.5 to 20 parts by weight relative to 100 parts by weight of the monomer mixture in the reaction solution. In another example, the content may be about 1 part by weight or more, 1.5 parts by weight or more, 2 parts by weight or more, 2.5 parts by weight or more, 3 parts by weight or more, 3.5 parts by weight or more, or 4 parts by weight or more or about 18 parts by weight or less, 16 parts by weight or less, 14 parts by weight or less, 12 parts by weight or less, 10 parts by weight or less, 9 parts by weight or less, 8 parts by weight or less, 7 parts by weight or less, or 6 parts by weight or less.

The content of the surfactant may be a content of the surfactant in the reaction solution in the first step or, when the surfactant is also included in the second step, may be a content based on the sum of the reaction solutions applied in the first and second steps, like the monomer mixture.

The reaction solution may be prepared by dispersing the monomer mixture and/or the surfactant in a solvent (e.g., aqueous solvent such as water). Therefore, the reaction solution may further include the solvent. The content of the solvent is not particularly limited but, in an example, may be adjusted so that the concentration of the monomer mixture in the solvent ranges from about 5 to 90% by weight.

A method of performing the first step by initiating polymerization of the above-described reaction solution is not particularly limited. For example, the first step may be performed by adding a known polymerization initiator to a reaction solution and controlling conditions so that polymerization may proceed by the initiator.

As such an initiator, a known initiator, for example, a known aqueous initiator, may be used and as the type thereof, potassium persulfate (KPS), ammonium persulfate (APS), sodium persulfate and/or hydrogen peroxide may be exemplified, but the present application is not limited thereto.

The content of the initiator is not particularly limited and may be appropriately adjusted according to purpose. A method of initiating polymerization by the initiator is not particularly limited. For example, when the initiator is a thermal initiator, a method of appropriately applying heat is applied and when the initiator is a photoinitiator, a method of appropriately applying light is used.

As described above, according to the method, the monomer mixture, the surfactant and the like are dispersed in the solvent to prepare a reaction solution, some of the reaction solution is subjected to seed polymerization of the first step, then the remainder is added to the product produced by the seed polymerization of the first step and the second step proceeds. In this case, the method may include, before the first step, dispersing the monomer mixture, the surfactant and the like in the solvent to prepare the entire reaction solution, setting aside some of the entire reaction solution for use as the reaction solution of the first step. The content of the set-aside reaction solution used in the first step is not particularly limited and, for example, about 1 to 10% by weight of the entire reaction solution may be used as the reaction solution of the first step.

The reaction solution added in the second step of the method of the present application may further include an aqueous solvent and a surfactant in addition to the monomer mixture. For example, when some of the above-described entire reaction solution is set aside to perform the first step and the set-aside portion is used in the second step, like the reaction solution of the first step, the reaction solution of the second step also includes the surfactant and the like. Also, even when a separate reaction solution is added in the second step instead of the application of the method, the surfactant may be included in the reaction solution of the second step.

The addition rate of the reaction solution in the second step may be controlled. By controlling the addition rate of the reaction solution, a polymer having a desired monomer composition and desired physical properties may be more effectively produced.

For example, the addition rate of the reaction solution in the second step may be adjusted to be slower than the reaction rate of the monomers.

The method of performing the second step by initiating polymerization by adding the reaction solution as described above is not particularly limited. For example, like the first step, the second step may be performed by adding a known polymerization initiator and a reaction solution and controlling conditions so that polymerization may proceed by the initiator. In this case, the type and content of an applicable initiator and the polymerization initiation method by the initiator are the same as described for the first step.

The method of preparing a polymer composition of the present application may further include, after the first and second steps, a step of mixing the produced polymer with other necessary components such as the formaldehyde-removing agent and the like.

The present application also provides a film-forming agent and a cosmetic composition or a cosmetic, which include the above-described polymer. When the above-described polymer is used, a film-forming agent and the like, which are capable of forming a uniform film (coating) by application, exhibit high stability even when applied to skin, are excellent in oil resistance, anti-smudging properties and anti-powder flaking properties and include a minimized content of a harmful component, may be provided.

Therefore, the polymer may be applied in the manufacture of a film-forming agent or a cosmetic composition that may be used to manufacture various cosmetics such as beauty packs, makeup products applied around the mouth or eyes such as mascara and the like, nail polish applied to fingernails or toenails, lipstick, eye shadow, hair styling products, eyeliner and the like. In addition, the polymer, the film-forming agent, or the like may be applied for pharmaceutical use due to the above-described characteristics and as pharmaceutical use, a bandage, a transdermal absorption preparation, or the like may be exemplified.

The content of the polymer in the film-forming agent, cosmetic composition, or cosmetic is not particularly limited and may be selected in consideration of applications and the like. For example, when the polymer is applied to the cosmetic composition, the content of the polymer in the composition may range from 1% by weight to 20% by weight, but the present application is not limited thereto.

The film-forming agent, cosmetic composition, or cosmetic may further include other active components according to applications. As the additional active components, a cosmetic component for whitening, UV protection, or the like, a medicinal component, a physiologically active component, or a pharmacologically active component may be exemplified. As such an active component, a local anesthetic component (lidocaine, dibucaine hydrochloride, dibucaine, ethyl aminobenzoate, etc.), an analgesic component (salicylic acid derivatives such as methyl salicylate, indomethacin, piroxicam, ketoprofen, pervinac, etc.), an anti-inflammatory component (glycyrrhetinic acid, glycyrrhizic acid salts such as dipotassium glycyrrhizinate, glycyrrhetic acid, stearyl glycyrrhetinate, bufexamac, benzyl nicotinate, hydrocortisone, hydrocortisone butyrate, hydrocortisone acetate, prednisone valeroacetate, prednisone acetate, prednisone, dexamethasone, dexamethasone acetate, dimethyl isopropyl azulene ibuprofenpiconol, arnica extracts, Scutellaria Baicalensis root extracts, cattail ear extracts, chamomile extracts, calamine, licorice extracts, guaiazulene, gardenia extracts, gentiana extracts, black tea extracts, tocopherol, tocopherol acetate, lithospermum extracts, perilla extracts, peony extracts, sage extracts, Swertia japonica extracts, Mulberry root extracts, pyridoxine hydrochloride, peach leaf extracts, cornflower extracts, Saxifraga extracts, mugwort extracts, Roman chamomile extracts, etc.), an anti-histamine component (chlorpheniramine maleate, diphenhydramine, diphenhydramine hydrochloride, diphenhydramine salicylate, ISO penzyl hydrochloride, etc.), a local irritation component (ammonia, 1-menthol d1-canfull, peppermint oil, benzyl nicotinate, nonylic acid vanillylamide, etc.), an antipruritic component (crotamiton etc.), a preservative or sterilizing component (acrinol, chlorhexidine gluconate, chlorhexidine hydrochloride, benzalkonium chloride, benzethonium chloride, povidone iodine, iodoform, iodine, potassium iodide, merbromin, oxides, cresol, triclosan, phenol, isopropyl methyl phenol, thymol, sodium salicylate, undecylenic acid, photosensitizers, hinokitiol, phenoxyethanol, chlorobutanol, quaternium-73, zinc pyrithione, p-oxybenzoic acid esters, *eucalyptus* extracts, resorcin rosemary extracts, etc.), an antifungal component (imidazole-based antifungal agents such as clotrimazole, clotrimazole acetate, miconazole acetate, econazole acetate, bifornazole, oxiconazole acetate, sulconazole acetate, neticonazole hydrochloride, bifornazole, tioconazole and omoconazole acetate; allylamine-based antifungal agents such as terbinafine, terbinafine hydrochloride and naftifine; benzylamine-based antifungal agents such as butenafine; allylamine-based antifungal agents such as amorphin hydrochloride; thiocarbamic acid-based antifungal agents such as tolnaftate and tolciclate; pyrrolnitrin, exalamide, ciclopirox olamine, etc.), a tissue-repairing component (allantoin, heparin-like substances, vitamin A palmitate, vitamin D2, retinol acetate, retinol, vitamin A oil, panthenol, etc.), an astringent component (zinc oxide, Acanthopanax senticosus extracts, aluminum chloride, yellow gourd extracts, salts thereof, citric acid, white birch extracts, tea extracts, hop extracts, horse chestnut extracts, etc.), a dead skin-softening component (urea, glycerin, concentrated glycerin, potassium hydroxide, salicylic acid, sulfur, colloidal sulfur, resorcin, glycolic acid, lactic acid, sodium sulfate, etc.), a moisturizing component (butylene glycol, sodium pyrrolidone carboxylate, propylene glycol, ribonucleic acid sodium, Angelica utilis extracts, asparaginic acid, alanine, arginine, sodium alginate, althaea extracts, aloe vera extracts, oyster extracts, hydrolyzed keratin, hydrolyzed collagen, hydrolyzed conchiolin, hydrolyzed egg shell membrane, hydrolyzed albumen, hydrolyzed silk, brown algae extracts, quince extracts, bramble extracts, xylitol, chitosan, cucumber extracts, quince seed extracts, glycine, glycerin, glucose, cape aloe extracts, cystin, cysteine, mallow extracts, serine, sorbitol, trehalose, sodium lactate, sodium hyaluronate, placenta extracts, sponge gourd extracts, multi-function materials, mannitol, lily extracts, lactoferrin, lysine, apple extracts, royal jelly extracts, etc.), an emollient component (almond oil, avocado oil, olive oil, oleic acid, orange roughy oil, cacao butter, carrot extracts, squalane, ceramide, evening primrose oil, grape seed oil, jojoba oil, macadamia nut oil, mineral oil, mink oil, eucalyptus oil, rosehip oil, Vaseline, etc.), a whitening component (ascorbic acid, ascorbic acid derivatives, arbutin, rucinol, ellagic acid, glutathione, kojic acid, rose fruit extracts, kiwi extracts, etc.), a UV protective component (p-aminobenzoic acid, ethyl esters of p-aminobenzoic acid, glycerin esters of p-aminobenzoic acid, amyl alcohol esters of p-dimethylaminobenzoic acid, 2-ethylhexyl alcohol esters of p-dimethylaminobenzoic acid, t-butylmethoxydibenzoyl methane, oxybenzones, octyl triazone, octyl salicylate, ethyl diisopropyl cinnamate, methyl diisopropyl cinnamate, cinoxate, dimethoxy cinnamic acid glyceryl octanate, octyl dimethoxy benzylidene dioxoimidazolidine propionate, Chinese tea extracts, drometrizole, isopropyl p-methoxycinnamate, homosalate, octyl methoxy cinnamate, etc.), a herbal extract component, a vitamin, an amino acid, a mineral, or the like may be exemplified, but the present application is not limited thereto.

The film-forming agent, cosmetic composition, or cosmetic may further include other solvents, additives, or the like according to applications.

As the solvent, for example, alcohols (e.g., polyethylene glycol, etc.), ethers (other than diethyl ether, glycol ethers (cellosolves such as methyl cellosolve, dialkylene glycol alkyl ethers such as diethylene glycol ethyl ether), etc.), nitriles (acetonitrile, etc.), ketones (acetone, etc.), or esters (carboxylic acid alkyl esters such as ethyl acetate, etc.) may be exemplified according to the use and use form of the composition and the like.

In addition, as the additive, not only plasticizers, wetting agents, antifoaming agents, coloring agents, preservatives, aromatics, flavors, pigments or thickeners but also common components used in quasi-drugs, pharmaceuticals, or cosmetics, for example, powdery base materials or carriers (binders, disintegrants, excipients, lubricants, etc.), oily base materials or carriers (animal and vegetable oils, waxes, Vaseline, paraffin oils, silicone oils, higher fatty acid esters, higher fatty acids, etc.), aqueous base materials or carriers (gel base materials such as xanthan gum, etc.), preservatives, chelating agents, antioxidants, refreshing agents, stabilizers, fluidizers, emulsifiers, thickeners, buffering agents, dispersing agent, absorbents, moisturizing agents, wetting agents, desiccants, antistatic agents, or other resins (polyamide-based resins, olefin-based resins such as hydrogenated polybutene, etc.) may be exemplified, but the present application is not limited thereto.

A method of manufacturing the film-forming agent, cosmetic composition, or cosmetic using the above-described components or, if necessary, other known additional components is not particularly limited and a known method may be used.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
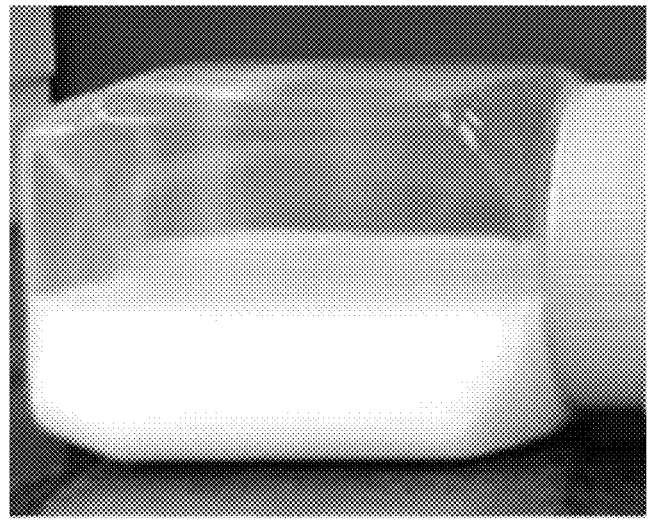
FIGS. 1 and 2 are images obtained by photographing polymers prepared in Examples 3 and 4, respectively.

Hereinafter, the polymer and the like of the present application will be described in detail with reference to examples and comparative examples. However, it should be understood that the examples disclosed herein are not intended to limit the scope of the polymer and the like. Physical properties in the examples and comparative examples were evaluated by the following methods.

1. Measurement of Methanol and Formaldehyde Contents

A methanol content was confirmed via gas chromatography-flame ionization detector (GC-FID). As a measuring instrument, 7890B GC System commercially available from Agilent Technologies, Inc. was used. A sample was diluted in acetonitrile (ACN) and then a methanol content was confirmed. Measurement conditions for the confirmation of a methanol content were as follows.

<Measurement Conditions>
Measuring instrument: 7890B GC System (Agilent Technologies, Inc.)
Column: HP-FFAP (19091F-115) (50 m*320 μm*0.5 μm)
Injector temperature: 220° C.
Oven temperature: 60° C./10 min-25° C./min-220° C./13 min
Flow rate: 1.5 mL/min
Injection volume: 1.5 μL injection A formaldehyde content was confirmed via liquid chromatography-UV (LC-UV). As a measuring instrument, 1260 Infinity II LC commercially available from Agilent Technologies, Inc. was used. A sample was obtained by standardization with water and one-hour ultrasonic extraction and then a formaldehyde content was confirmed. Measurement conditions for the confirmation of a formaldehyde content were as follows.

<Measurement Conditions>
Column: C18 (5 μm, 4.6*250 mm)
Mobile phase: ACN:Water=60:40
Oven temperature: 30° C.
Injection volume: 10 μL
Detection: 360 nm 2. Measurement of Molecular Weight A weight-average molecular weight (Mw) and a molecular weight distribution (PDI) were measured under the following conditions through gel permeation chromatography (GPC) and for making a calibration curve, measurement results were converted using standard polystyrene of Agilent System.

<Measurement Conditions>
Measuring instrument: Agilent GPC (Agilent 1200 series, U.S.)
Column: PL Mixed B two connected
Column temperature: 40° C.
Eluent: Tetrahydrofuran (THF)
Flow rate: 1.0 mL/min
Concentration: ~1 mg/mL (100 μL injection)

3. Calculation of Glass Transition Temperature

A glass transition temperature (Tg) was calculated by the following Equation according to a monomer composition.

$$1/Tg = \Sigma Wn/Tn \qquad \text{<Equation>}$$

In the equation, Wn is a weight fraction of each monomer in the polymer, Tn is a glass transition temperature exhibited when the monomer has formed a homopolymer and the right-hand side of the equation is a result obtained by calculating the value (Wn/Tn) obtained by dividing the weight fraction of the used monomer by the glass transition temperature exhibited when the monomer has formed a homopolymer for each monomer and then summing all the calculated values.

4. Smudging Evaluation

A smudging evaluation was performed as follows. First, a sample (in a mascara formulation) was applied onto a glass plate to a thickness of about 100 μm and then dried at 25° C. for 24 hours. Afterward, 0.1 g of artificial sebum was dropped onto an about 4 cm$^2$ area of the dried sample, wetting proceeded for 10 minutes, paper was placed thereon and a horizontal reciprocating motion with a weight of 500 g was performed 20 times. Then, the degree of artificial sebum staining of the paper was subjected to image analysis.

As the artificial sebum, artificial sebum containing triglycerides at 40% by weight, diglycerides at 2.2% by weight, free fatty acids at 16.4% by weight, squalene at 12% by weight, wax esters at 25% by weight, cholesterol at 1.4% by weight and cholesterol esters at 2% by weight was used.

Through the image analysis, a result obtained by dividing the color difference measurement value of the paper including artificial sebum dropped thereonto after the sample was applied and dried by the color difference measurement value of a paper including artificial sebum dropped thereonto while the sample formulation was not applied was confirmed and a higher resulting value indicates better anti-smudging properties.

5. Powder Flaking Evaluation

A powder flaking evaluation was performed as follows. First, a mascara formulation was applied 10 times to human hair strands and dried and the dried human hair sample was immersed in a 25° C. distilled water for 5 seconds and then taken out. The human hair sample was dried for 3 minutes and then powder that flaked off by rubbing the human hair sample 20 times with an amplitude of about 2 cm using a nylon brush was compared by image analysis. A powder flaking value is a value obtained by measuring the number of pieces of powder that flake off when human hair strands are coated with the formulation, dried, then immersed in water, taken out and rubbed.

6. Panel Evaluation

A mascara use test was conducted by 20 expert evaluation panelists (25 to 50 years old). After 6 hours of application of mascara to the panelists, the degrees of smudging (sebum staining) and powder flaking were evaluated by the following criteria based on an average of one to five point scores.

<Evaluation Criteria for Smudging and Powder Flaking>
A: 4.5 points or more on average
B: 3.5 points or more and less than 4.5 points on average
C: 2.5 points or more and less than 3.5 points on average
D: less than 2.5 points on average
<Point Evaluation Criteria>
<Smudging Evaluation>
5 point: no smudging
4 point: slight smudging
3 point: moderate smudging
2 point: severe smudging
1 point: extreme smudging
<Powder Flaking Evaluation>
5 point: no powder flaking
4 point: slight powder flaking
3 point: moderate powder flaking
2 point: severe powder flaking
1 point: extreme powder flaking Example 1

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 10 g of acrylic acid (solubility parameter: 13.6 $(cal/cm^3)^{1/2}$, Tg: 105° C.), 110 g of 2-ethylhexyl acrylate (solubility parameter: 8.8 $(cal/cm^3)^{1/2}$, Tg: −50° C.), 80 g of ethyl methacrylate (solubility parameter: 9.7 $(cal/cm^3)^{1/2}$, Tg: 65° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. Through the above-described process, a polymer polymerization solution with excellent phase stability and no increase in viscosity was obtained. The obtained polymerization solution had a molecular weight (Mw) of about 500,000 to 650,000 and a Tg of about −8.6° C. Then, the polymerization solution was mixed with 5 g of an aqueous ammonia solution (28% by weight) as a formaldehyde-removing agent to prepare a polymer composition. Subsequently, the polymer composition was mixed with other components as shown in Table 1 below to obtain a mascara formulation. The figures shown in Table 1 below are weight ratios.

Example 2

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 10 g of methacrylic acid (solubility parameter: 12.3 $(cal/cm^3)^{1/2}$, Tg: 225° C.), 115 g of 2-ethylhexyl acrylate (solubility parameter: 8.8 $(cal/cm^3)^{1/2}$, Tg: −50° C.), 75 g of ethyl methacrylate (solubility parameter: 9.7 $(cal/cm^3)^{1/2}$, Tg: 65° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. Through the above-described process, a polymer polymerization solution with excellent phase stability and no increase in viscosity was obtained. The obtained polymerization solution had a molecular weight (Mw) of about 500,000 to 650,000 and a Tg of about −9.0° C. Then, the polymerization solution was mixed with 5 g of an aqueous ammonia solution (28% by weight) as a formaldehyde-removing agent to prepare a polymer composition. Subsequently, the polymer composition was mixed with other components as shown in Table 1 below to obtain a mascara formulation.

Example 3

200 g of purified water and 2.5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 30 g of 2-hydroxyethyl acrylate (solubility parameter: 14.1 $(cal/cm^3)^{1/2}$, Tg: −15° C.), 90 g of 2-ethylhexyl acrylate (solubility parameter: 8.8 $(cal/cm^3)^{1/2}$, Tg: −50° C.), 80 g of ethyl methacrylate (solubility parameter: 9.7 $(cal/cm^3)^{1/2}$, Tg: 65° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. FIG. 1 is an image of a polymer polymerization solution obtained through the above-described process. Through the above-described process, a polymer polymerization solution with excellent phase stability and no increase in viscosity was obtained. The obtained polymerization solution had a molecular weight (Mw) of about 500,000 to 650,000 and a Tg of about −9° C. Then, the polymerization solution was mixed with 4 g of an aqueous ammonia solution (28% by weight) as a formaldehyde-removing agent to prepare a polymer composition. Subsequently, the polymer composition was mixed with other components as shown in Table 1 below to obtain a mascara formulation.

Comparative Example A 200 g of purified water and 2.5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

Figure 2:
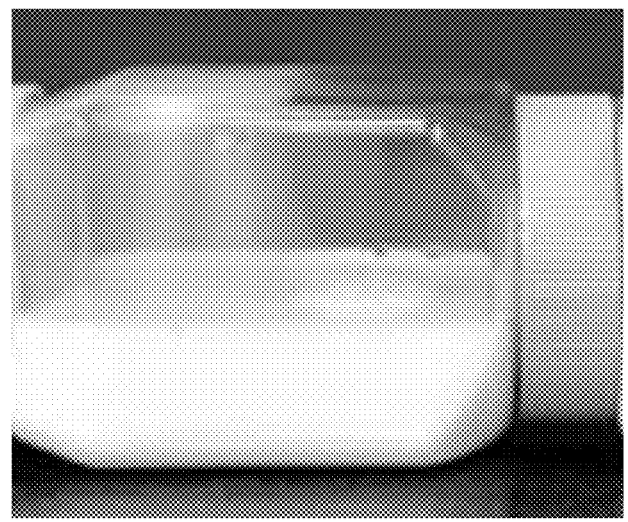

100 g of purified water, 30 g of 2-hydroxyethyl acrylate (solubility parameter: 14.1 $(cal/cm^3)^{1/2}$, Tg: −15° C.), 55 g of 2-ethylhexyl acrylate (solubility parameter: 8.8 $(cal/cm^3)^{1/2}$, Tg: −50° C.), 115 g of methyl methacrylate (solubility parameter: 10.1 $(cal/cm^3)^{1/2}$, Tg: 105° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. FIG. 2 is an image of a polymer polymerization solution obtained through the above-described process. Through the above-described process, a polymer polymerization solution with excellent phase stability and no increase in viscosity was obtained. The obtained polymerization solution (polymer composition) had a molecular weight (Mw) of about 500,000 to 650,000 and a Tg of about 26.5° C. Subsequently, the polymer composition was mixed with other components as shown in Table 1 below to obtain a mascara formulation.

Comparative Example 1

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 120 g of 2-ethylhexyl acrylate (solubility parameter: 8.8 $(cal/cm^3)^{1/2}$, Tg: −50° C.), 80 g of methyl methacrylate (solubility parameter: 10.1 $(cal/cm^3)^{1/2}$, Tg: 105° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. The obtained polymerization solution (polymer composition) had a molecular weight (Mw) of about 500,000 to 650,000 and a Tg of about −6.2° C. Subsequently, the polymer composition was mixed with other components as shown in Table 1 below to obtain a mascara formulation.

TABLE 1

|  | Examples | | | | Comparative Example |
|---|---|---|---|---|---|
|  | 1 | 2 | 3 | 4 | 1 |
| Polymer composition | 30 | 30 | 30 | 30 | 30 |
| Water | 44.4 | 44.4 | 44.4 | 44.4 | 44.4 |
| Disodium EDTA | 0.1 | 0.1 | 0.1 | 0.1 | 0.1 |
| Butylene glycol | 5 | 5 | 5 | 5 | 5 |
| Triethanolamine | 1 | 1 | 1 | 1 | 1 |
| Phenoxy ethanol | 0.5 | 0.5 | 0.5 | 0.5 | 0.5 |
| Hydroxyethyl cellulose | 0.5 | 0.5 | 0.5 | 0.5 | 0.5 |
| Iron oxides (CI77499) | 5 | 5 | 5 | 5 | 5 |
| Stearic acid | 5 | 5 | 5 | 5 | 5 |
| Beeswax | 6 | 6 | 6 | 6 | 6 |
| Copernicia cerifera (carnauba) wax | 2 | 2 | 2 | 2 | 2 |
| Polyglyceryl-3 beewax | 0.5 | 0.5 | 0.5 | 0.5 | 0.5 |

The results of evaluation of physical properties for each of Examples and Comparative Example were summarized in the following Table 2 (In Table 2, a methanol content and a formaldehyde content are for the polymer composition and the units thereof are ppm).

TABLE 2

|  | Examples | | | | Comparative Example |
|---|---|---|---|---|---|
|  | 1 | 2 | 3 | 4 | 1 |
| Methanol content | not detected | not detected | not detected | 21 | 23 |
| Formaldehyde content | 2.3 | 3.5 | 3.3 | 37.5 | 36.5 |
| Smudging test | 94.3 | 93.9 | 97.3 | 96.6 | 51.6 |
| Powder flaking test | 4 | 3 | 4 | 11 | 3 |
| Smudging (panel evaluation) | A | B | A | A | D |
| Powder flaking (panel evaluation) | B | A | B | D | A |

Reference Example 1

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 10 g of acrylic acid (solubility parameter: 13.6 (cal/cm$^3$)$^{1/2}$, Tg: 105° C.), 110 g of 2-ethylhexyl acrylate (solubility parameter: 8.8 (cal/cm$^3$)$^{1/2}$, Tg: −50° C.), 80 g of ethyl methacrylate (solubility parameter: 9.7 (cal/cm$^3$)$^{1/2}$, Tg: 65° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. The obtained polymerization solution (polymer composition) had a Tg of about −8.6° C. As a result of confirming the polymer composition in the same manner as in Examples and Comparative Example, methanol was not detected and a formaldehyde content was about 20.8 ppm.

Reference Example 2

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 10 g of acrylic acid (solubility parameter: 13.6 (cal/cm$^3$)$^{1/2}$, Tg: 105° C.), 60 g of 2-ethylhexyl acrylate (solubility parameter: 8.8 (cal/cm$^3$)$^{1/2}$, Tg: −50° C.), 130 g of ethyl methacrylate (solubility parameter: 9.7 (cal/cm$^3$)$^{1/2}$, Tg: 65° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. The obtained polymerization solution (polymer composition) had a Tg of about 21.1° C. As a result of measuring the methanol and formaldehyde contents of the polymer composition in the same manner as in Examples and Comparative Example, methanol was not detected and a formaldehyde content was about 21.6 ppm. In addition, results of the smudging test, powder flaking test, smudging test (panel evaluation) and powder flaking test (panel evaluation) for a mascara formulation obtained in the same manner as Example 1 except for using the polymer composition were 93.4, 10, B and D, respectively.

Reference Example 3

200 g of purified water and 5 g of sodium hydrogen carbonate (saturated; neutralizing agent) were input into a reactor 1 equipped with a cooler, a nitrogen inlet, a thermometer and a stirrer and uniformly mixed and a temperature inside the reactor was raised up to 70° C.

100 g of purified water, 10 g of acrylic acid (solubility parameter: 13.6 (cal/cm$^3$)$^{1/2}$, Tg: 105° C.), 85 g of 2-ethylhexyl acrylate (solubility parameter: 8.8 (cal/cm$^3$)$^{1/2}$, Tg: −50° C.), 105 g of methyl methacrylate (solubility parameter: 10.1 (cal/cm$^3$)$^{1/2}$, Tg: 105° C.), 4 g of sodium lauryl sulfate and 4 g of Triton X-405 were input into a reactor 2 equipped with a separate stirrer and emulsified. 5% by weight of the emulsion in the reactor 2 was separated and input into the reactor 1, 0.5 g of an initiator (ammonium persulfate) was added and seed polymerization was performed for 30 minutes. The emulsion remaining in the reactor 2 after the seed polymerization was input into the reactor 1. During the input of the emulsion remaining in the reactor 2, 0.5 g of an initiator (ammonium persulfate) dissolved in purified water was also added and polymerization was performed for 24 hours. In this process, the input rate of the emulsion was controlled to about 85 mL/min. The obtained polymerization solution (polymer composition) had a Tg of about 18.8° C. As a result of measuring the methanol and formaldehyde contents of the polymer composition in the same manner as in Examples and Comparative Example, methanol and formaldehyde contents were 19 ppm and 38.1 ppm, respectively. In addition, results of the smudging test, powder flaking test, smudging test (panel evaluation) and powder flaking test (panel evaluation) for a mascara formulation obtained in the same manner as Example 1 except for using the polymer composition were 95.5, 14, A and D, respectively.

Reference Example 4

Figure 3:
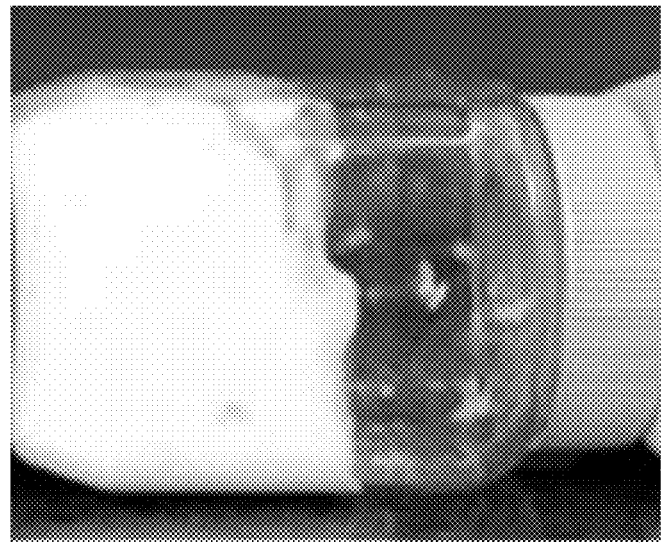
FIGS. 3 and 4 are images obtained by photographing polymers prepared in Reference Examples 4 and 5, respectively.

300 g of purified water, 30 g of 2-hydroxyethyl acrylate (solubility parameter: 14.1 (cal/cm$^3$)$^{1/2}$, Tg: −15° C.), 90 g of 2-ethylhexyl acrylate (solubility parameter: 8.8 (cal/cm$^3$)$^{1/2}$, Tg: −50° C.), 80 g of ethyl methacrylate (solubility parameter: 9.7 (cal/cm$^3$)$^{1/2}$, Tg: 65° C.), 4 g of sodium lauryl sulfate, 4 g of Triton X-405 and 2.5 g of saturated sodium hydrogen carbonate as a neutralizing agent were input into a reactor equipped with a cooler, a nitrogen inlet, a thermometer and a stirrer and emulsified and a temperature inside the reactor was raised up to 70° C. Afterward, 1 g of an initiator (ammonium persulfate) was added and polymerization was performed for 24 hours. The obtained polymerization solution had a Tg of about −9° C. FIG. 3 is an image of the polymer polymerization solution obtained through the above-described process.

Reference Example 5

Figure 4:
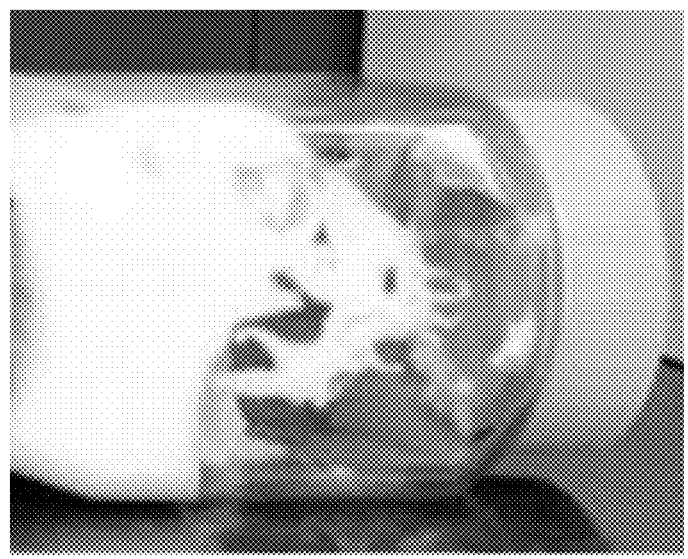

300 g of purified water, 30 g of 2-hydroxyethyl acrylate (solubility parameter: 14.1 (cal/cm$^3$)$^{1/2}$, Tg: −15° C.), 55 g of 2-ethylhexyl acrylate (solubility parameter: 8.8 (cal/cm$^3$)$^{1/2}$, Tg: −50° C.), 115 g of methyl methacrylate (solubility parameter: 10.1 (cal/cm$^3$)$^{1/2}$, Tg: 105° C.), 4 g of sodium lauryl sulfate, 4 g of Triton X-405 and 2.5 g of saturated sodium hydrogen carbonate as a neutralizing agent were input into a reactor equipped with a cooler, a nitrogen inlet, a thermometer and a stirrer and emulsified and a temperature inside the reactor was raised up to 70° C. Afterward, 1 g of an initiator (ammonium persulfate) was added and polymerization was performed for 24 hours. The obtained polymerization solution had a Tg of about 26.5° C. FIG. 4 is an image of the polymer polymerization solution obtained through the above-described process.

The present application is directed to providing a polymer composition, which has excellent oil resistance and is capable of forming a cosmetic or the like that has no smudging and no powder flaking during use and a film-forming agent and a cosmetic manufactured using the same.

What is claimed is:

1. A cosmetic composition, comprising a polymer, a moisturizing agent, a wax and a pigment:
   wherein the polymer comprising polymerization units of a first monomer and a second monomer,
   wherein a homopolymer of the first monomer has a solubility parameter of 11.0 $(cal/cm^3)^{1/2}$ or more
   wherein a homopolymer of the second monomer has a solubility parameter of less than 11.0 $(cal/cm^3)^{1/2}$
   wherein an amount of the polymerization unit of the first monomer in the polymer is from 1 to 40% by weight,
   wherein the polymer comprises the polymerization unit of the second monomer in an amount of 150 to 4,000 parts by weight relative to 100 parts by weight of the polymerization unit of the first monomer,
   wherein the polymerization unit of the second monomer comprises a polymerization unit of a monomer A having a glass transition temperature of 20° C. or more and a polymerization unit of a monomer B having a glass transition temperature of less than 20° C., and
   wherein a weight ratio (A/B) of the polymerization unit of the monomer A and the polymerization unit of the monomer B is from 0.25 to 5.

2. The cosmetic composition according to claim 1, wherein an amount of methanol in the polymer is 30 ppm or less.

3. The cosmetic composition according to claim 1, wherein an amount of formaldehyde in the polymer is 30 ppm or less.

4. The cosmetic composition according to claim 1, wherein the first monomer has a glass transition temperature of −40° C. to 400° C.

5. The cosmetic composition according to claim 1, wherein the first monomer is a hydroxyl group-containing monomer, a polymeric heterocyclic monomer, a (meth) acrylamide-based monomer, an acidic monomer, glyceryl (meth)acrylate, or an alkylene oxide unit-containing monomer.

6. The cosmetic composition according to claim 1, wherein the second monomer is represented by the following Chemical Formula 3:

[Chemical Formula 3]

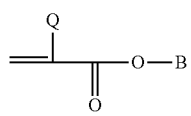

wherein Q is hydrogen or an alkyl group and B is a straight or branched alkyl group having 2 or more carbon atoms, an alicyclic hydrocarbon group, or an aromatic substituent.

7. The cosmetic composition according to claim 1, wherein the polymer has a glass transition temperature of −30° C. to 30° C.

8. The cosmetic composition according to claim 1, wherein the polymer has a weight-average molecular weight of 100,000 to 2,000,000.

9. The cosmetic composition according to claim 1, wherein the polymer is a seed emulsion polymer.

10. The cosmetic composition according to claim 1, further comprising a formaldehyde-removing agent.

11. A method of preparing the cosmetic composition according to claim 1, comprising:
    a first step of performing seed emulsion polymerization of a reaction solution comprising a monomer mixture, an aqueous solvent and a surfactant; and
    a second step of growing a seed produced in the first step by adding a reaction solution containing a monomer mixture to the product produced by the seed emulsion polymerization and performing emulsion polymerization,
    wherein each of the monomer mixtures of the first step and the second step comprises a first monomer and a second monomer,
    wherein a homopolymer of the first monomer has a solubility parameter of 11.0 $(cal/cm^3)^{1/2}$ or more and a homopolymer of the second monomer has a solubility parameter of less than 11.0 $(cal/cm^3)^{1/2}$,
    wherein an amount of the first monomer in the monomer mixtures of the first step and the second step is from 4 to 40% by weight and
    wherein the second monomer is comprised in an amount of 150 to 4,000 parts by weight relative to 100 parts by weight of the first monomer in the monomer mixtures of the first step and the second step
    wherein the polymerization unit of the second monomer comprises a polymerization unit of a monomer A having a glass transition temperature of 20° C. or more and a polymerization unit of a monomer B having a glass transition temperature of less than 20° C., and
    wherein a weight ratio (A/B) of the polymerization unit of the monomer A and the polymerization unit of the monomer B is from 0.25 to 5.

12. The method of claim 11, further comprising, before the first step, a step of mixing a monomer mixture, an aqueous solvent and a surfactant to prepare a reaction solution and setting aside some of the entire reaction solution for use as the reaction solution of the first step.

13. The method of claim 11, further comprising a step of mixing the polymerization product resulting from the second step with a formaldehyde-removing agent.

14. A cosmetic composition, comprising a polymer, a moisturizing agent, a wax and a pigment:
    wherein the polymer comprising polymerization units of a first monomer and a second monomer,
    wherein a homopolymer of the first monomer has a solubility parameter of 11.0 $(cal/cm^3)^{1/2}$ or more,
    wherein a homopolymer of the second monomer has a solubility parameter of less than 11.0 $(cal/cm^3)^{1/2}$,
    wherein an amount of the polymerization unit of the first monomer in the polymer is from 1 to 40% by weight,
    wherein the polymer comprises the polymerization unit of the second monomer in an amount of 150 to 4,000 parts by weight relative to 100 parts by weight of the polymerization unit of the first monomer,
    wherein the polymerization unit of the second monomer comprises a polymerization unit of a monomer A having a glass transition temperature of 20° C. or more and a polymerization unit of a monomer B having a glass transition temperature of less than 20° C.,
    wherein a weight ratio (A/B) of the polymerization unit of the monomer A and the polymerization unit of the monomer B is from 0.25 to 5, and
    wherein the polymer does not include a polymerization unit of a methanol-producing monomer.

15. The cosmetic composition according to claim 14, wherein the methanol-producing monomer is methyl (meth) acrylate.

\* \* \* \* \*